(12) United States Patent
Sedlmayr et al.

(10) Patent No.: US 11,278,308 B2
(45) Date of Patent: Mar. 22, 2022

(54) BLADE FOR A CUTTING INSTRUMENT, SCALPEL HOLDER FOR A BLADE, AND METHOD FOR PRODUCING A BLADE

(71) Applicant: Robert Bosch GmbH, Stuttgart (DE)

(72) Inventors: Andreas Sedlmayr, Pforzheim (DE); Uwe Glanz, Asperg (DE); Inga Schellenberg, Karlsruhe (DE); Thomas Loibl, Oberstdorf (DE); Imke Heeren, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 1030 days.

(21) Appl. No.: 14/993,282

(22) Filed: Jan. 12, 2016

(65) Prior Publication Data

US 2016/0199086 A1 Jul. 14, 2016

(30) Foreign Application Priority Data

Jan. 13, 2015 (DE) ...................... 10 2015 200 308.6

(51) Int. Cl.
| | | |
|---|---|---|
| *A61B 17/3209* | (2006.01) | |
| *A61B 18/08* | (2006.01) | |
| *B23P 15/28* | (2006.01) | |
| *A61B 17/3211* | (2006.01) | |
| *A61B 17/00* | (2006.01) | |
| *A61B 18/00* | (2006.01) | |
| *A61B 18/12* | (2006.01) | |

(52) U.S. Cl.
CPC ...... *A61B 17/3209* (2013.01); *A61B 17/3211* (2013.01); *A61B 18/082* (2013.01); *B23P 15/28* (2013.01); *A61B 2017/00084* (2013.01); *A61B 2018/00041* (2013.01); *A61B 2018/0091* (2013.01); *A61B 2018/00107* (2013.01); *A61B 2018/00607* (2013.01); *A61B 2018/00714* (2013.01); *A61B 2018/126* (2013.01); *A61B 2218/002* (2013.01); *A61B 2218/007* (2013.01)

(58) Field of Classification Search
CPC ...... A61B 18/1492; A61B 2018/00065; A61B 2018/1472; A61B 2090/065; A61B 2218/002; A61B 2218/007
See application file for complete search history.

(56) References Cited

U.S. PATENT DOCUMENTS

| | | | | |
|---|---|---|---|---|
| 3,768,482 A | * | 10/1973 | Shaw | A61B 18/082 606/29 |
| 3,826,263 A | * | 7/1974 | Cage | G05D 23/2401 606/31 |
| 4,089,336 A | * | 5/1978 | Cage | A61B 18/08 219/233 |
| 4,091,813 A | * | 5/1978 | Shaw | A61B 18/08 219/233 |

(Continued)

FOREIGN PATENT DOCUMENTS

| | | |
|---|---|---|
| DE | 44 07 797 A1 | 9/1995 |
| DE | 296 1 8 309 U1 | 1/1997 |

(Continued)

*Primary Examiner* — Tigist S Demie

(74) *Attorney, Agent, or Firm* — Maginot, Moore & Beck LLP

(57) ABSTRACT

A blade for a cutting instrument, in particular for medical use, includes a first ceramic layer, a second ceramic layer, and a heating device arranged between the first ceramic layer and the second ceramic layer.

17 Claims, 7 Drawing Sheets

(56) References Cited

U.S. PATENT DOCUMENTS

| | | | | |
|---|---|---|---|---|
| 4,485,810 A | * | 12/1984 | Beard | A61B 17/3213 219/228 |
| 4,622,966 A | * | 11/1986 | Beard | A61B 17/3213 219/233 |
| 4,862,890 A | * | 9/1989 | Stasz | A61B 18/1402 606/48 |
| 5,308,311 A | * | 5/1994 | Eggers | A61B 17/3211 600/28 |
| 5,925,039 A | * | 7/1999 | Landingham | A61B 18/14 606/41 |
| 6,132,427 A | * | 10/2000 | Jones | A61B 18/1402 606/41 |
| 6,171,275 B1 | * | 1/2001 | Webster, Jr. | A61B 18/1492 600/374 |
| 6,409,725 B1 | * | 6/2002 | Khandkar | A61B 18/14 606/29 |
| 6,511,479 B2 | * | 1/2003 | Gentelia | A61B 18/1402 606/39 |
| 2001/0012936 A1 | * | 8/2001 | Heim | A61B 18/14 606/45 |
| 2002/0116022 A1 | * | 8/2002 | Lebouitz | A61B 17/32 606/167 |
| 2005/0273097 A1 | * | 12/2005 | Ryan | A61B 18/1442 606/45 |

FOREIGN PATENT DOCUMENTS

| | | |
|---|---|---|
| EP | 2 392 281 A1 | 12/2011 |
| FR | 1.414.590 | 9/1965 |
| WO | 93/21838 A1 | 11/1993 |
| WO | 94/09714 A1 | 5/1994 |
| WO | 2008/094564 A2 | 8/2008 |

\* cited by examiner

BLADE FOR A CUTTING INSTRUMENT, SCALPEL HOLDER FOR A BLADE, AND METHOD FOR PRODUCING A BLADE

This application claims priority under 35 U.S.C. § 119 to patent application no. DE 10 2015 200 308.6, filed on Jan. 13, 2015 in Germany, the disclosure of which is incorporated herein by reference in its entirety.

BACKGROUND

The present disclosure relates to a blade for a cutting instrument, in particular for medical use, to a corresponding scalpel holder for a blade, and to a method of producing a corresponding blade.

In certain medical interventions, cuts are made, the edges of said cuts being cauterized in order to stop the blood flow. Cauterization can take place, ideally, instantaneously, so as to minimize blood loss and to make it easier for the doctor to see the area on which he is working. Use is currently made, for example, of electric scalpels. These function as follows: a current is conducted through the human body and, as a result of heating, leads to cauterization by coagulation of the proteins, as a result of which veins and tissue are welded. A distinction is made between monopolar electric scalpels and bipolar electric scalpels.

In the case of the monopolar variety (main application), one pole of the voltage source is connected to the patient over the largest surface area possible. The knife forms the second pole. It may be the case here that the current, rather than flowing specifically to the site which is to be cauterized, also finds another way through the patient's body, or over the surface of the patient's body, and this results in severe burning at the incorrect site.

In the case of the bipolar variety, the two poles are arranged on the tool, for example tweezers or forceps. Reference is made here to bipolar tool designs such as scissors or forceps.

The formation of fluid (blood, tissue fluid, etc.) which nevertheless occurs obscures the view and is removed via an additional suction-extraction tool.

SUMMARY

Against this background, the approach in question here presents a blade for a cutting instrument, in particular for medical use, a corresponding scalpel holder for a blade, and a method of producing a blade. Advantageous configurations can be gathered from the Drawings, Claims and the following Description.

The disclosure presents a ceramic knife which has an internal heater and can be heated before or during the cutting process. In this way then, coagulation take place at the same time as cutting (resection), without this resulting in undesired quantities of blood escaping. It is optionally possible, in addition, to integrate a means for extracting fluid by suction and for metering fluid or introducing fluid for drug-release purposes. If a channel level with the spine of the knife is fitted with the opening in the direction of the tip of the knife, it would also be possible, for example, to blow in air or some other gas or therapeutic aerosol.

The disclosure presents a blade for a cutting instrument, in particular a blade for medical use, characterized by a first ceramic layer, a second ceramic layer and a heating device, which is arranged between the first ceramic layer and the second ceramic layer.

A cutting instrument can be understood to mean a scalpel or a surgical instrument for cutting through tissue. The blade can be understood to mean a blade of a heatable scalpel for instantaneous coagulation. The cutting instrument may thus be a fine knife with a very sharp blade. The blade may have a cutting edge, two opposite sides, which adjoin the cutting edge, a to spine and a stem. It is possible here for the heating device to be arranged between the two blade sides. The heating device may be arranged in the region of the cutting edge. In one embodiment, it is also possible for the blade to have more than one cutting edge. The blade is advantageously biocompatible; in particular in comparison with a metal blade, it is possible for the blade described here to be extremely biocompatible. It is possible for the blade to have a longer service life than a metal scalpel, and thus to remain sharp over a long period of use, or over a longer period of use in comparison with a metal scalpel. There is advantageously no current flowing through a human body when the blade is used medically for cutting through tissue.

The first ceramic layer and the second ceramic layer may be connected to form a monolithic component. It is thus possible to achieve a high level of stability.

The heating device may have at least one connection which is exposed in relation to the second ceramic layer. This means that electrical contact can easily be made with the heating device. The connection may thus comprise at least one contact pad. In the favorable embodiment, the heating device may have at least two contact pads for making electrical contact, said pads remaining uncovered by the second layer.

It is also possible for the first ceramic layer and in addition, or as an alternative, the second ceramic layer to be produced, at least in part, from a green ceramic film. The first ceramic layer and in addition, or as an alternative, the second ceramic layer may have zirconium oxide.

The heating device may comprise a temperature-measuring device. It is thus possible to regulate a temperature of the blade. It is also possible for the heating device to have a heating wire for heating up the blade a number of times to above 500° C. In particular it is possible for a material thickness of the heating wire, or a material of the heating wire, to be suitable for heating up the blade a number of times to above 500° C. The heating wire may be designed in the form of a heating meander.

At least one fluid channel may be formed between the first ceramic layer and the second ceramic layer. A fluid channel can be understood to mean a channel, a tube or a cavity. In a particular embodiment, it is possible for the blade to have two fluid channels or more than two fluid channels. The fluid channel may be designed here to transport a fluid such as a body fluid or a drug, a flushing medium or therapeutic fluid. It is thus possible for the blade to have at least one collecting channel, from which a plurality of fluid channels branch off. The integrated cavities in the form of fluid channels may advantageously allow specific extraction of fluids by suction or else also introduction of flushing medium or drugs.

The at least one fluid channel may have at least one opening in the form of an inlet and in addition, or as an alternative, an outlet for a fluid in the region of a cutting edge and in addition, or as an alternative, of a blade side and in addition, or as an alternative, a blade spine and in addition, or as an alternative, a stem of the blade. Extraction of fluids by suction or else also introduction of flushing medium or drugs may advantageously be made possible via the at least one opening of the at least one fluid channel.

A cross section of the fluid channel may have a diameter in a tolerance range between 0.20 and 3 mm. It is thus possible for the cross section to be adapted to a viscosity and to a flow behavior of a fluid which is to be conducted. The cross section of the fluid channel may be adapted to a geometry of the blade.

The cross section of the fluid channel may be circular, ellipsoidal or slot-shaped at least in certain regions. It is thus possible for a first portion to be round and for a second portion to be, for example, ellipsoidal or slot-shaped. It is thus possible for different portions of the fluid channel to be formed differently from one another. The at least one opening of the fluid channel may be circular, ellipsoidal or slot-shaped. A second opening may be formed differently to a first opening. It is thus possible for the opening and the cross section of the fluid channel to be adapted to a viscosity and to a flow behavior of a fluid which is to be conducted.

A plane in which the heating device is arranged can run through a cutting edge of the blade. In particular the blade may be formed symmetrically in relation to the plane which runs through the cutting edge. It is possible for the blade to be combined with a standard scalpel holder.

The disclosure presents a scalpel holder for a variant of a blade in question here for a cutting instrument, wherein the scalpel holder has at least one connection for making contact with the heating device of the blade.

The scalpel holder may have a fluid connection for fluid-feeding and/or fluid-removal purposes for the fluid channel of the blade. It is possible for the fluid connection to be coupled to an opening of the fluid channel. It is thus possible for the fluid connection to be oriented in relation to an opening of the fluid channel of the blade.

The scalpel holder may have an energy store, in particular for operating the heating device. It is also possible for the scalpel holder to have at least one tank for a fluid. The tank may be connected to the fluid connection via a pump.

The disclosure presents a method of producing a blade for a cutting instrument, wherein the method comprises the following steps:

arranging in place a first ceramic-forming material layer for generating a first ceramic layer; arranging a heating device on the first ceramic-forming material layer and/or the first ceramic layer;

arranging a second ceramic-forming material layer, for generating a second ceramic layer, on the first ceramic-forming material layer, and therefore the heating device is arranged between the first ceramic-forming material layer and the second ceramic-forming material layer;

tempering the arrangement made up of the first and second ceramic-forming material layers with the heating device, wherein the first ceramic layer and the second ceramic layer enclose the heating device; and grinding the sintered arrangement to obtain the blade for the cutting instrument or a surgical instrument.

A ceramic-forming material layer can be understood to mean, for example, a green film or a layer of ceramic injection molding. The tempering step can be understood to mean sintering or debinding. It is possible here for the arrangement to be heated, for example, to above 1200° C. In the tempering step, the ceramic-forming material layers can be converted into the ceramic layers.

The ceramic-forming material layer described here may be produced, for example, in the form of green films via slip casting. They form an "endless product", which is subsequently separated by a cutting process. As an alternative, it would also be possible for the ceramic-forming material layers to be produced, via ceramic injection molding, in the form of specific moldings and for these then to be printed with the heating meanders and for two matching parts to be laminated together or, following the printing, to be overmolded in a repeated injection-molding operation. A very high level of design freedom would be available here.

The approach in question here also creates an apparatus which is designed to implement, activate and/or realize the steps of a variant of a method in question here in corresponding devices. It is also the case that this variant of the disclosure in the form of an apparatus allows the object on which the disclosure is based to be achieved quickly and efficiently.

One aspect of the present disclosure is the realization of a heatable ceramic knife using ceramic multilayer technology. Ceramic multilayer technology is used, for example, in the production of ceramic exhaust sensors (for example lambda sensors).

It is advantageously possible for the inert, ceramic blade to be heated directly via the internal heater without heater material here being in direct contact with the patient's body. The ceramic blade material here is advantageously extremely biocompatible. The service life of the material is advantageously longer than that of metal scalpels, since the blade remains sharp over a long period of use. It is possible to achieve sterilization to above the inherent temperature of the knife. It is thus possible to provide for an increase in temperature to above 500° C. and thus to clean the knife of adhering tissue remnants or the like by pyrolysis. There is advantageously no current flowing through the body—no collateral damage during an operation. The integrated cavities in the form of channels optionally allow extraction of fluids by suction or else also introduction of flushing medium or drugs.

BRIEF DESCRIPTION OF THE DRAWINGS

The approach in question here will be explained in more detail by way of example below with reference to the accompanying Drawings, in which.

DETAILED DESCRIPTION

The following description of advantageous exemplary embodiments of the present disclosure uses the same or similar designations for the similarly acting elements illustrated in the various figures, repetition of the description of these elements being dispensed with.

Figure 1:
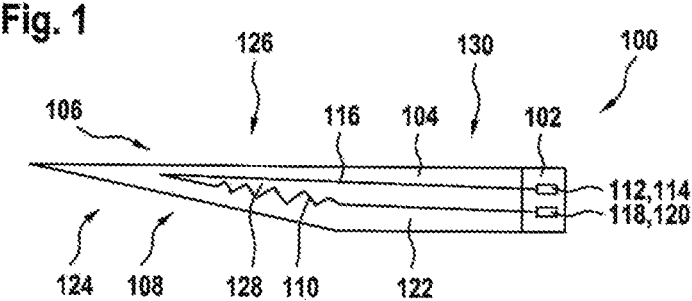
FIG. 1 shows a simplified illustration of a blade according to one exemplary embodiment of the present disclosure.

FIG. 1 shows a simplified illustration of a blade 100 according to one exemplary embodiment of the present disclosure. The blade 100 has a first ceramic layer 102, a second ceramic layer 104 and a heating device 106, which is arranged between the first ceramic layer 102 and the second ceramic layer 104.

In the exemplary embodiment illustrated, the heating device 106 comprises a heating meander 110 as a heating element 108, a first contact pad 112 as a first connection 114, a first supply line 116 between the first contact pad 112 and the heating meander 110, a second contact pad 118 as a second connection 120, and a second supply line 122 between the second contact pad 118 and the heating meander 110. The second ceramic layer 104 is smaller than the first ceramic layer 102, and therefore the connections 114, 120 are exposed and contact can easily be made therewith. The heating meander 110 can be understood to mean a heating wire, a heater meander or a temperature meander.

In a particular exemplary embodiment, the heating device 106 comprises a heating element 108 made of platinum with a high-resistance heating meander 110 and low-resistance supply lines 116, 112. The high-resistance heating meander 110 consists, for example, of a platinum alloy with palladium or rhodium.

In one exemplary embodiment, the first ceramic layer 102 and the second ceramic layer 104 are connected to form a monolithic component or a monolithic ceramic body. In one exemplary embodiment, the ceramic body of the blade 100 has a layer-like construction, wherein the heating meander 110 and the supply lines 116, 112 are applied to individual ceramic films by means of screen printing.

The blade has a cutting edge 124, a spine 126, a side 128 and a stem 130. The shape of the cutting edge 124 is described in more detail in FIG. 6. In a particular exemplary embodiment, the blade is, for example, a clip point blade or a drop point blade. The stem 130 may be designed to be connected to a scalpel holder, as is described in more detail, for example, in FIGS. 7 and 8.

Figure 2:
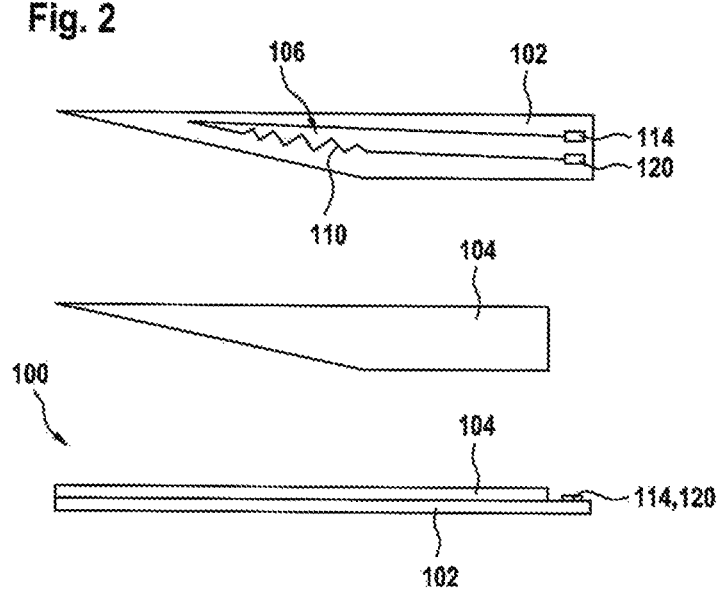
FIG. 2 shows a simplified illustration of the ceramic layers and of the heating device according to one exemplary embodiment of the present disclosure.

FIG. 2 shows a simplified illustration of the ceramic layers 102, 104 and of the heating device 106 according to one exemplary embodiment of the present disclosure. The ceramic layers 102, 104 and the heating device 106 and also the blade 100 may be a variant of an exemplary embodiment of a blade 100, of the ceramic layers 102, 104 and of the heating device 106 which is illustrated in FIG. 1.

FIG. 2 shows the parts of a blade 100 in three associated illustrations. The first ceramic layer 102 with the heating device 106 arranged thereon is illustrated at the top of FIG. 2. The heating device 106 here has two connections 114, 120. The heating device 106 comprises a heating meander 110 in the region of the cutting edge 124. The second ceramic layer 104 is shown in the central image of FIG. 2. The bottom image of FIG. 2 shows a section taken transversely to the ceramic layers 102, 104 illustrated, in which case it is possible to see the exposed connections 114, 120.

Figure 3:
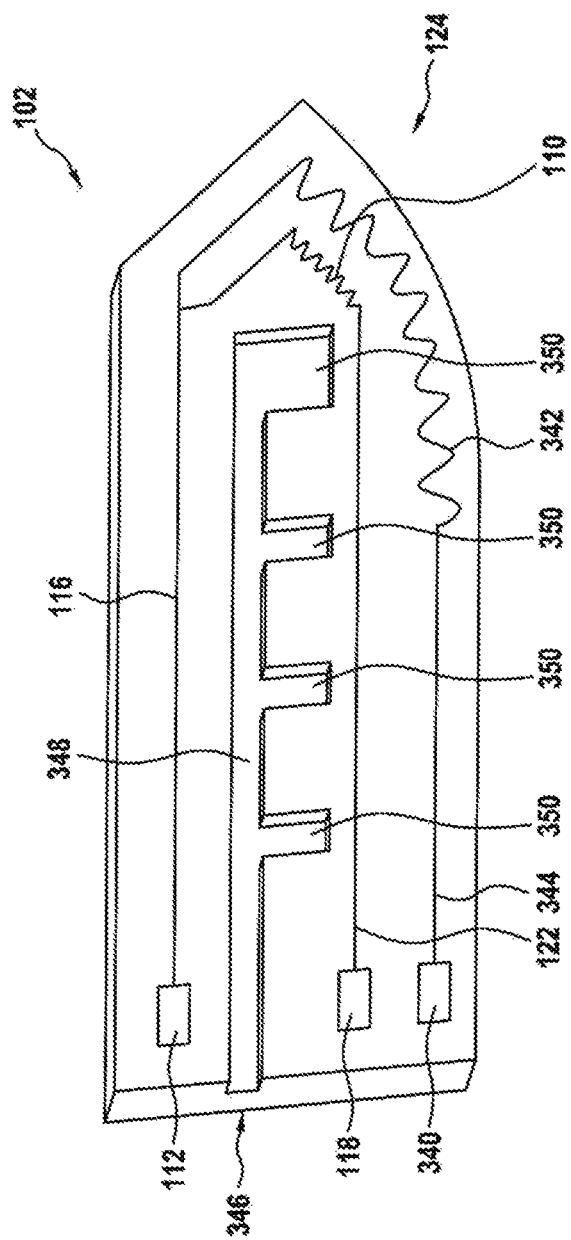
FIG. 3 shows a simplified illustration of a first ceramic layer according to one exemplary embodiment of the present disclosure.

FIG. 3 shows a simplified three-dimensional illustration of a first ceramic layer 102 according to one exemplary embodiment of the present disclosure. The first ceramic layer 102 may be a variant of an embodiment of a first ceramic layer 102 which is shown in the previous figures. A heating device 102 is arranged on a surface of the first ceramic layer 102. The heating device 106 comprises a first contact pad 112, a second contact pad 118 and a third contact pad 340, a first heating meander 110 and a second heating meander 342, a first supply line 116 between the first contact pad 108 and the first and second heating meanders 110, 342, a second supply line 122 between the second contact pad 118 and the first heating meander 110, and a third supply line 344 between the third contact pad 340 and the second heating meander 342.

Depending on the exemplary embodiment, the supply lines 116, 122, 344 have a width between 100 µm and 400 µm and a thickness between 5 µm and 20 µm. Depending on the exemplary embodiment, the heating meanders 110, 342 have a width between 40 µm and 100 µm and a thickness between 2 µm and 20 µm.

A fluid channel 346 is arranged in the first ceramic layer 102. A collecting channel 348 of the fluid channel 346 runs essentially along a main direction of extent of the first ceramic layer 102.

Four metering channels 350 branch off from the collecting channel 348, essentially transversely to the collecting channel 348, in the direction of the cutting edge 124 of the blade, that is to say in the downward direction in the illustration. The metering channels 350 form, as it were, blind alleys, and these lead to openings in the second ceramic layer, said openings being illustrated in the following figure, FIG. 4. The number of channels, however, is not fixed; depending on requirements, it is possible to vary the number of channels or the position thereof.

In one exemplary embodiment, the fluid channel 346 is a suction-extraction channel 346.

In one exemplary embodiment, the fluid channel 346 has a height between 0.1 mm and 3 mm and a depth between 0.1 mm and 0.8 mm.

In one exemplary embodiment, the first heating meander 110 is configured in the form of a temperature meander.

Figure 4:
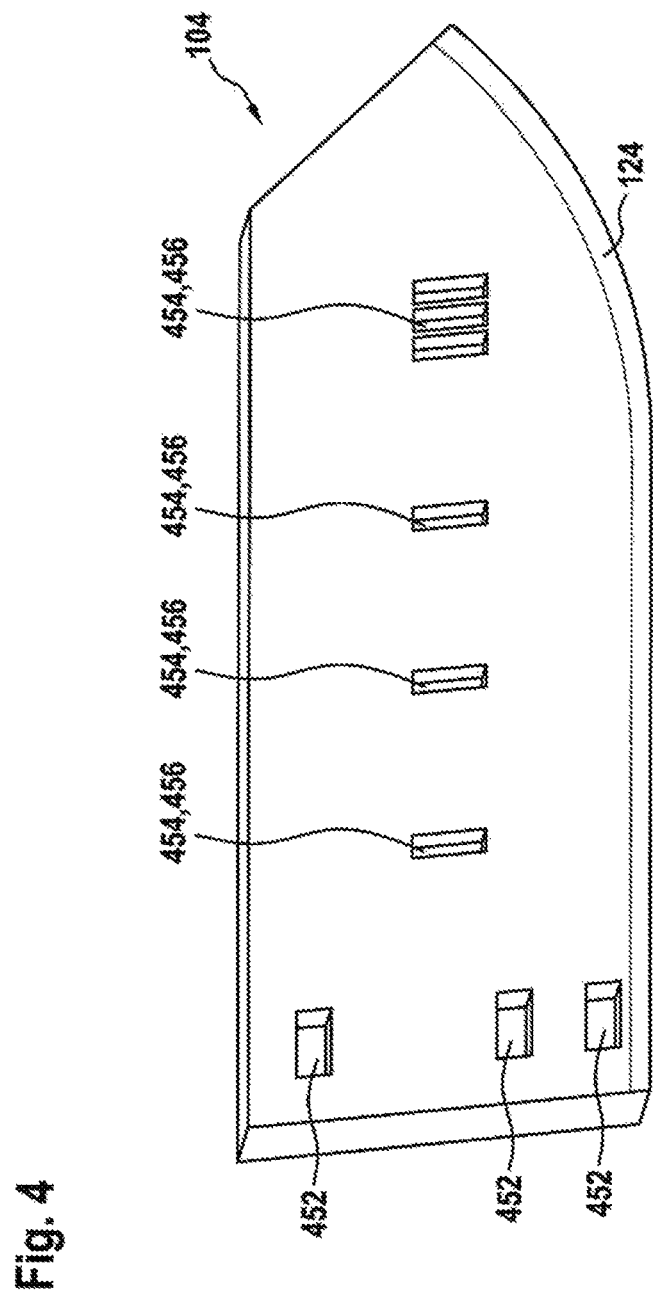
FIG. 4 shows a simplified illustration of a second ceramic layer according to one exemplary embodiment of the present disclosure.

FIG. 4 shows a simplified illustration of a second ceramic layer 104 according to one exemplary embodiment of the present disclosure. The second ceramic layer 104 may be a variant of an exemplary embodiments of a second ceramic layer 104 which is shown in FIGS. 1 and 2. As illustrated in the following figure, FIG. 5, the second ceramic layer 104 can be combined with the ceramic layer 102, which is illustrated in FIG. 3, to form a blade 100.

Figure 5:
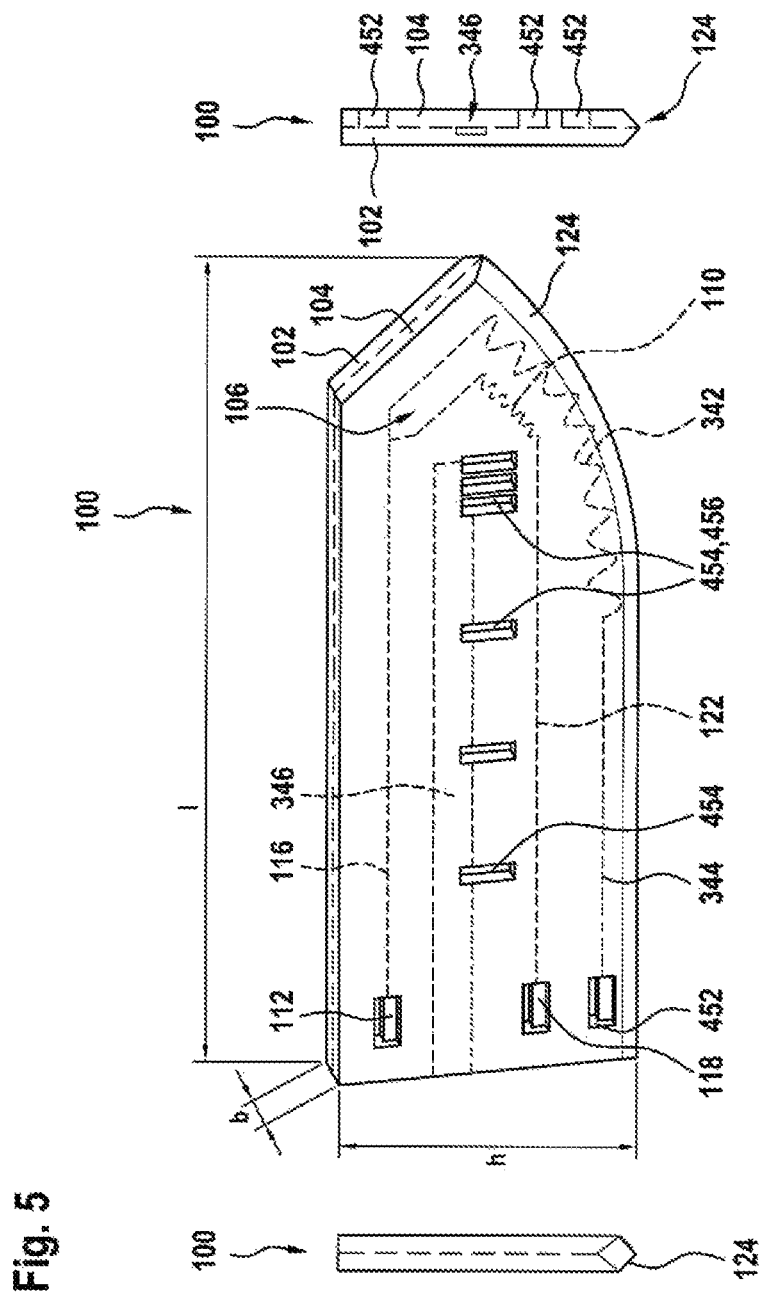
FIG. 5 shows a simplified illustration of a blade according to one exemplary embodiment of the present disclosure.

The second ceramic layer 104 has a plurality of through-passages 452, 454. Three through-passages 452 are positioned such that the connections 114, 120 or contact pads 112, 118, 340 arranged on the first ceramic layer 102, which is illustrated in FIG. 3, are exposed when the two ceramic layers 102, 104 are joined together, as illustrated in FIG. 5. Furthermore, through-passages 454 are positioned in the form of inlet or outlet openings 456 for a fluid in the region of the blade side. The through-passages 454 are arranged to correspond with the metering channels 350, which are illustrated in FIG. 3. The slot-shaped formation of the openings 456 leads the latter also to be referred to as shark gills. One metering channel here is assigned three openings 456, and the other metering channels are assigned one opening 456 each.

In one exemplary embodiment, the through-passages 452 have a length between 1 mm and 4 mm and a width between 0.5 mm and 2 mm. In an alternative exemplary embodiment, the openings 456 have a length between 0.1 mm and 3.5 mm and a width between 0.1 mm and 3.5 mm.

FIG. 5 shows a simplified illustration of a blade 100 according to one exemplary embodiment of the present disclosure. The blade 100 may be a variant of an exemplary embodiment of a blade 100 which is shown in FIGS. 1 and 2. The blade 100 comprises a first ceramic layer 102 and a second ceramic layer 104 and also a heating device 106, which is arranged between the ceramic layers. The ceramic layers 102, 104 are the first ceramic layer 102, which is illustrated in FIG. 3, and the second ceramic layer 104, which is illustrated in FIG. 4. The blade 100 is illustrated in a plan view on the left, in a side view in the center and in a rear view on the right. The plan view, which is illustrated on the left, shows, in particular, a shape of the cutting edge 124 of the blade 100. Variants of the cutting edge 124 are illustrated by way of example in FIG. 6.

In the centrally illustrated side view of the blade 100, the second ceramic layer 104 with the through-passages 452, 454 is arranged, and illustrated, in front of the first ceramic layer 102. A heating device 106 is arranged between the first ceramic layer 102 and the second ceramic layer 104. A fluid channel 346 in the first ceramic layer 102 is connected to the openings 456 in the second ceramic layer 104. The through-passages 452 are arranged such that the contact pads 112, 118, 340 are exposed and contact can be made therewith.

The dimensions of the blade 100 vary in different exemplary embodiments. The blade here has, for example, a length l between 15 mm and 50 mm, a width b between 0.25 mm and 1 mm and a height h between 5 mm and 20 mm.

The rear view, which is illustrated on the right, shows a connection for the fluid channel 346 and also the through-passages 452 in the second ceramic layer 104.

The depth of the through-passages 452 extends as far as the contact pads 112, 118, 340 or the corresponding connections.

The dimensions indicated in FIGS. 3 to 5 are dependent, inter alia, on the geometry of the knife or on the geometry and the dimensions of the blade 100.

The heatable knife is characterized by a heating meander and a temperature meander (for example platinum) being embedded between two green ceramic films (for example zirconium oxide). For example the heating meander and the connection contacts here are applied to a green ceramic film (un-sintered) via screen printing.

In one exemplary embodiment, following a drying step, a second green film can be applied and, via a laminating process in a hot press, connected intimately to the first film.

Since the knife does not have any sensitive measuring cell like a lambda sensor, it is possible to dispense with, for example, heater insulation that includes printed aluminum-oxide layers in the case of the lambda sensor, as a result of which the production process becomes relatively straightforward.

In one exemplary embodiment, the aforementioned second green film is shaped, prior to being covered, such that the connection contacts on the printed film are not covered over.

Figure 6:
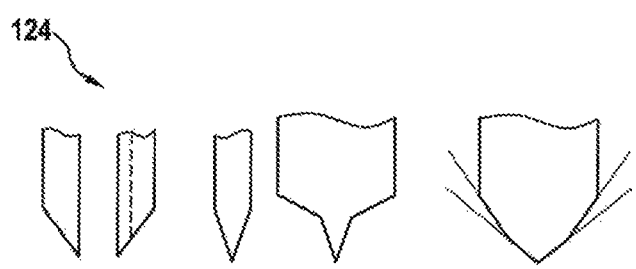
FIG. 6 shows a simplified illustration of shapes of the cutting edge according to one exemplary embodiment of the present disclosure.

FIG. 6 shows a simplified illustration of shapes of the cutting edge 124 according to exemplary embodiments of the present disclosure. The cutting edge 124 may be a detail of a variant of a blade 100 illustrated in FIG. 1, 2 or 5. FIG. 6 shows, by way of example, five variants of cutting edge 124. In this figure, as illustrated from left to right, the first two cutting edges 124 are ground on one side, the central cutting edge is ground centrally to form the blade with straight cutting surfaces and the final two cutting edges are double-ground centrally. The lateral cutting surfaces here are straight, convex or concave or a combination thereof. It is therefore the case that the final cutting edge 124, starting from the tip, is first of all of concave shape, which then merges into a convex shape.

The position of the boundary surface between the first ceramic layer and the second ceramic layer in relation to the cutting edge varies in different exemplary embodiments.

Figure 7:
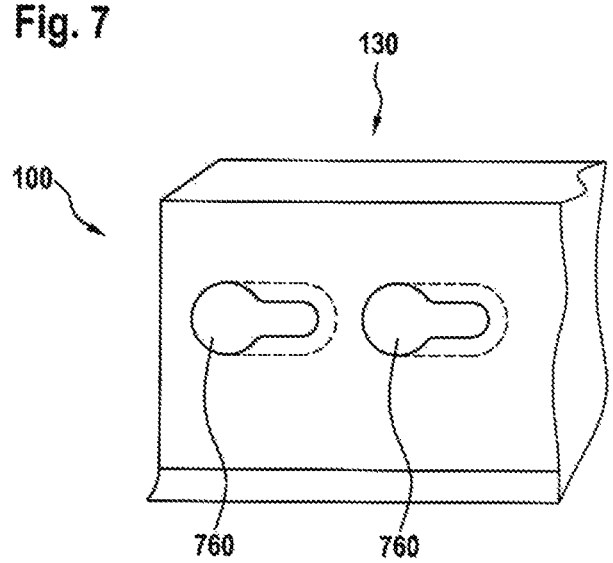
FIG. 7 shows a simplified illustration of a quick-fit fastener for the blade according to one exemplary embodiment of the present disclosure.

FIG. 7 shows a simplified illustration of a quick-fit fastener 760 for the blade 100 according to one exemplary embodiment of the present disclosure. The blade 100 may be an exemplary embodiment of a blade 100 described in the previous figures. The stem 130 of a blade 100 has two quick-fit fasteners 760 in order to connect the blade 100 to a scalpel holder. The quick-fit fastener 760 is an exemplary embodiment of a coupling device for coupling the blade 100 mechanically to a scalpel holder.

Figure 8:
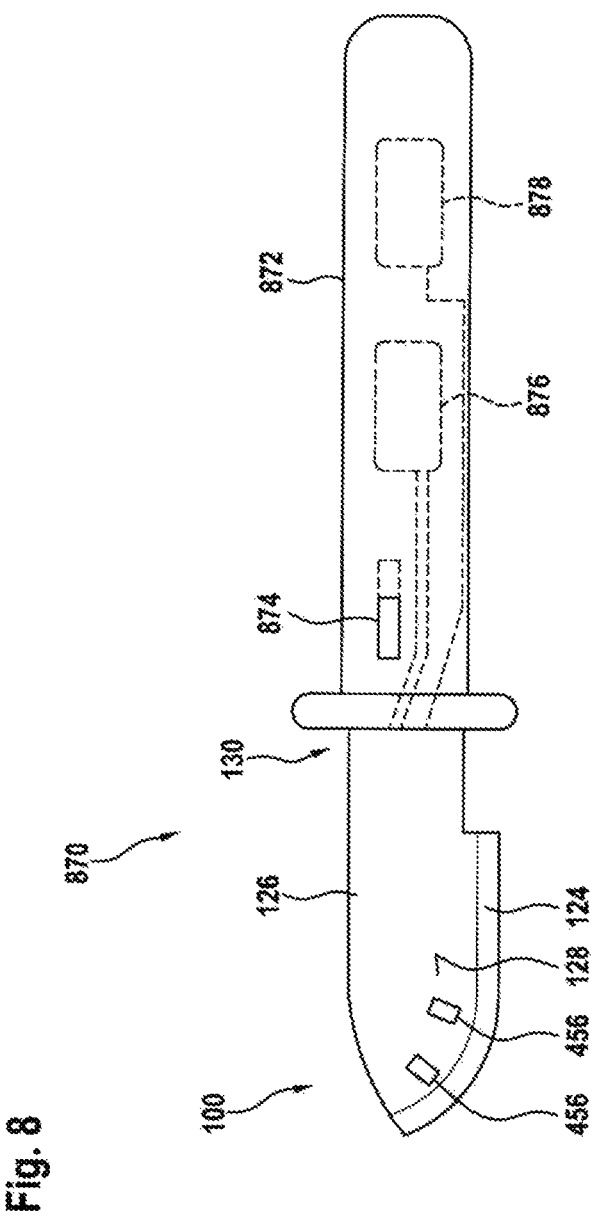
FIG. 8 shows a simplified illustration of a cutting instrument having a blade and a scalpel holder according to one exemplary embodiment of the present disclosure.

FIG. 8 shows a simplified illustration of a cutting instrument 870 having a blade 100 and a scalpel holder 872 according to one exemplary embodiment of the present disclosure. The blade 100 may be a variant of a blade 100 described in the previous figures. The blade 100 has a cutting edge 124, a spine 126 and a stem 130. Two openings 456 adjoin the cutting edge 124 at least on the visible blade side 128. In the region of the stem 130, the blade 100 is coupled, or connected, mechanically to the scalpel holder 872. The scalpel holder 872 has a locking device 874, a tank 876 and an energy store 878. The tank 876 is connected to a fluid channel of the blade 100 via a fluid channel formed in the scalpel holder. The energy store 878 is connected, via appropriate lines, to the connections of the heating device arranged in the blade 100.

In an exemplary embodiment which is not illustrated, a pump for delivering a fluid is arranged between the tank 876 and the connection of the tank, via a fluid channel, to the blade 100.

Instead of an energy store 878 or a tank 876, it is also possible to provide an interface for the connection of an external fluid line or of an electric power supply.

The scalpel holder 872 has a connection for making contact with the heating device 106 of the blade 100. The scalpel holder illustrated also has an optional fluid connection for fluid-feeding and/or fluid-removal purposes. Contact can thus easily be made with the heating device of the blade 100 and the fluid channel of the blade 100.

In one exemplary embodiment, the blade 100 and the scalpel holder 872 can be coupled using an adapted or extended system such as the known standard system, BAYHA system, OR system or gouge system. The systems here can be extended by the connections for the heating device and in addition, or as an alternative, for the fluid channel.

Depending on the exemplary embodiment, the cutting instrument 870 may be, for example, a heatable scalpel for instantaneous coagulation or a heatable knife with integrated channels for extracting media by suction, or for feeding media, in medicine.

Figure 9:
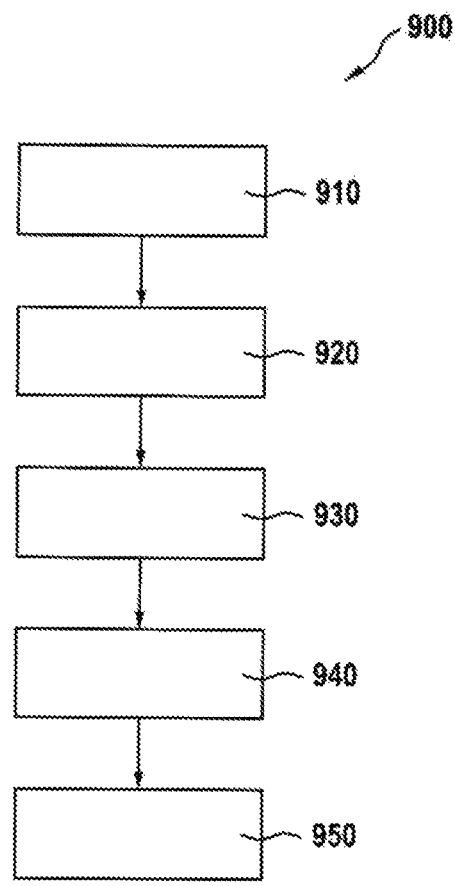
FIG. 9 shows a flow chart of a method according to one exemplary embodiment of the present disclosure.

FIG. 9 shows a flow chart of a method 900 according to one exemplary embodiment of the present disclosure. The method 900 of producing a blade for a cutting instrument comprises three arranging steps 910, 920, 930, a tempering step 940 and a grinding step 950.

Step 910 arranges in place a first green film for generating a first ceramic layer, step 920 arranges a heating device on the first ceramic layer and, finally, step 930 arranges a second green film, for generating a second ceramic layer, on the first green film and the heating device, and therefore the heating device is arranged between the first green film and the second green film.

This is followed, in tempering step 940, by the arrangement made up of the first and second green films with the heating device being subjected to de-binding and/or sintering to form the first ceramic layer and the second ceramic layer, which enclose the heating device. To conclude, in grinding step 950, the sintered arrangement is ground to obtain a blade for a surgical instrument. The blade may be a variant of a blade 100 shown and described in the preceding figures.

Cavities and through-passages can be made in a specific manner in the green film via a milling/drilling process. The second green film bears through-cavities (for example bores) for the inlet/outlet of fluids/drugs.

The channel-like cavities may be made in dimensions ranging from 0.25-3 mm. They may be circular and also slot-shaped. It is also conceivable for the openings to be routed obliquely through the material to the collecting channel in the interior, in order to achieve more advantageous flow conditions for the inlet/outlet operations and the internal channeling of media. As an alternative, the collecting channel may also be realized via screen printing. For this purpose, the channel-forming structures are printed using a purely organic thick-film paste, and this burns out completely during the de-binding operation. If the two green films are laminated by being fitted over one another and pressed with one another in the hot press, and if the laminate is subjected to de-binding, cavities remain at the location which previously had the purely organic paste printed on it. This makes it possible to provide very narrow and fine channel structures.

Apertures for the contact region are provided in the rear part of the knife. In a manner analogous to the ceramic exhaust sensors, printing can be carried out in multiple-up format, separation to give separate units also being carried out here prior to sintering.

Conversion into a monolithic component takes place in the subsequent sintering process at 1250° C.-1385° C. for 5 h. The blade may be of fully symmetrical design overall, and so no warping should be expected during sintering—this means that the high-outlay task of providing individual weighting for the parts during sintering may possibly also be dispensed with.

Following sintering, the blade is ground using known hard machining processes. It is then possible for the blade to have its unground central part clipped or plugged into a scalpel holder or also pressed into a housing (in a manner analogous to exhaust sensors being introduced into a round housing via sealing elements made of steatite), the connection contacts remaining exposed. The heater is connected via releasable metal clamps or contact clips, it also being possible here to make use of the contact-making techniques used for exhaust sensors.

It would be advantageous here to have a straightforward quick-fit plug-in system into a scalpel holder which is "easy to handle" for the doctor and, at the same time, constitutes the mechanical quick-fit fixing means and the electrical contact-making means and provides for extraction of media by suction and metering of media.

The exemplary embodiments described above and shown in the figures have been selected only by way of example. Entire different embodiments or individual features thereof can be combined with one another. It is also possible for one exemplary embodiment to be supplemented by features of a further exemplary embodiment.

It is also possible for the method steps in question here to be repeated and carried out in an order other than that described.

Where an exemplary embodiment comprises an "and/or" link between a first feature and a second feature, this should be read such that the exemplary embodiment, in one form, has both the first feature and the second feature and, in a further form, has either just the first feature or just the second feature.

What is claimed is:

1. A blade for a cutting instrument, comprising:
a first ceramic layer;
a second ceramic layer connected to the first ceramic layer so as to form a ceramic body; and
a heating device including a heating meander embedded in the ceramic body between the first ceramic layer and the second ceramic layer, the heating meander configured to generate heat at the first and second ceramic layers,
wherein the ceramic body defines a cutting edge of the blade, the cutting edge including at least one sharp edge.

2. The blade according to claim 1, wherein the ceramic body is a monolithic ceramic body.

3. The blade according to claim 1, wherein the heating device includes at least one contact connection that is exposed to an exterior of the blade.

4. The blade according to claim 1, wherein at least one of the first ceramic layer and the second ceramic layer at least one of:
(i) includes zirconium oxide; and
(ii) is formed from a green ceramic film.

5. The blade according to claim 1, wherein the heating device includes a temperature-measuring device.

6. The blade according to claim 1, wherein the heating device is positioned so as to lie along a plane that runs through the cutting edge of the blade.

7. The blade according to claim 6, wherein the blade is symmetrical about the plane.

8. The blade according to claim 1, wherein the blade is configured to be mounted on a scalpel holder.

9. The blade according to claim 1, wherein at least one of the first ceramic layer and the second ceramic layer includes zirconium oxide.

10. The blade according to claim 1, wherein the heating meander includes a heating wire that has at least one of a material thickness and a material composition that enables the blade to be repeatedly heated to a temperature above 500° C.

11. The blade according to claim 1, wherein the heating device further includes at least one supply line connected to the heating meander, the heating meander having a high electrical resistance as compared to the at least one supply line.

12. The blade according to claim 1, further comprising:
at least one fluid channel defined in the ceramic body and extending along a main direction of extent of the first ceramic layer.

13. The blade according to claim 12, wherein:
the second ceramic layer defines at least one opening fluidly connected to the at least one fluid channel so as to define at least one of an inlet and an outlet for a fluid; and
the at least one opening is located in a region of at least one of the cutting edge, a blade side, a blade spine, and a stem of the blade.

14. A blade for a cutting instrument, comprising:
a first ceramic layer;
a second ceramic layer connected to the first ceramic layer so as to form a monolithic ceramic body; and
a heating device including a heating meander embedded in the monolithic ceramic body between the first ceramic layer and the second ceramic layer, the heating meander configured to generate heat, wherein the monolithic ceramic body defines a cutting edge of the blade, the cutting edge including at least one sharp edge; and at least one fluid channel defined in the ceramic body and extending along a main direction of extent of the monolithic ceramic body.

15. The blade according to claim 14, wherein:

the second ceramic layer defines at least one opening fluidly connected to the at least one fluid channel so as to define at least one of an inlet and an outlet for a fluid; and the at least one opening is located in a region of at least one of the cutting edge, a blade side, a blade spine, and a stem of the blade.

16. The blade according to claim 15, wherein at least one of (i) the at least one fluid channel and (ii) the at least one opening has a cross section defined, at least in certain regions, by at least one of a circular shape, an ellipsoidal shape, and a slot shape.

17. The blade according to claim 14, the at least one fluid channel having a cross section with a diameter in a range from 0.25 mm to 3 mm.

\* \* \* \* \*